US009643920B2

United States Patent
Miyazaki et al.

(10) Patent No.: US 9,643,920 B2
(45) Date of Patent: May 9, 2017

(54) CRYSTALLINE 4-(3S-(1R-(1-NAPTHYL)ETHYLAMINO) PYRROLIDIN-1-YL)PHENYLACETIC ACID

(71) Applicant: MITSUBISHI TANABE PHARMA CORPORATION, Osaka-shi, Osaka (JP)

(72) Inventors: Hiroshi Miyazaki, Osaka (JP); Takao Komasaka, Osaka (JP); Joji Tsurumoto, Osaka (JP); Takeshi Uemura, Osaka (JP); Yuuji Morita, Osaka (JP)

(73) Assignee: MITSUBISHI TANABE PHARMA CORPORATION, Osaka (JP)

( * ) Notice: Subject to any disclaimer, the term of this patent is extended or adjusted under 35 U.S.C. 154(b) by 0 days.

(21) Appl. No.: 14/916,859

(22) PCT Filed: Sep. 5, 2014

(86) PCT No.: PCT/JP2014/073426
§ 371 (c)(1),
(2) Date: Mar. 4, 2016

(87) PCT Pub. No.: WO2015/034031
PCT Pub. Date: Mar. 12, 2015

(65) Prior Publication Data
US 2016/0200679 A1 Jul. 14, 2016

(30) Foreign Application Priority Data

Sep. 5, 2013 (WO) .................. PCT/JP2013/073954

(51) Int. Cl.
*C07D 207/50* (2006.01)
*C07D 207/14* (2006.01)

(52) U.S. Cl.
CPC ......... *C07D 207/50* (2013.01); *C07D 207/14* (2013.01)

(58) Field of Classification Search
CPC ........................... C07D 207/14; C07D 207/50
See application file for complete search history.

(56) References Cited

U.S. PATENT DOCUMENTS

2007/0225296 A1* 9/2007 Miyazaki ............. C07D 205/04
514/255.05
2010/0249049 A1* 9/2010 Miyazaki ............. C07D 205/04
514/25

(Continued)

FOREIGN PATENT DOCUMENTS

JP  8-12670 A  1/1996
JP  2011-6409 A  1/2011

(Continued)

OTHER PUBLICATIONS

Hirayama, "Yuki Kagobutsu Kessho Sakusei Handbook—Genri to Know How-", Maruzen Co., Ltd., 2008, pp. 101-102.

(Continued)

*Primary Examiner* — Valerie Rodriguez-Garcia
(74) *Attorney, Agent, or Firm* — Birch, Stewart, Kolasch & Birch, LLP

(57) ABSTRACT

The present invention provides crystal forms A and B of 4-(3S-(1R-(1-naphthyl)ethylamino)pyrrolidin-1-yl)phenylacetic acid having excellent stability and use as pharmaceutical ingredients. The present invention also provides industrially advantageous processes for producing these crystalline compounds.

11 Claims, 2 Drawing Sheets

(56) References Cited

U.S. PATENT DOCUMENTS

2011/0306776 A1    12/2011   Pomares et al.
2012/0115856 A1    5/2012   Ishikawa et al.

FOREIGN PATENT DOCUMENTS

| JP | 2012-511538 A | 6/2012 |
| WO | WO 2005/115975 A1 | 12/2005 |
| WO | WO 2009/107579 A1 | 9/2009 |

OTHER PUBLICATIONS

International Search Report issued in PCT/JP2014/073426, dated Nov. 18, 2014.

\* cited by examiner

CRYSTALLINE 4-(3S-(1R-(1-NAPTHYL)ETHYLAMINO)PYRROLIDIN-1-YL)PHENYLACETIC ACID

TECHNICAL FIELD

The present invention relates to crystalline arylalkylamine compounds that have an effect of activating calcium sensitive receptors (CaSR) and are useful as medicines, in particular, drugs for the prevention or treatment of diseases such as hyperparathyroidism, and to processes for producing the same.

BACKGROUND ART

The phenomenon existing in two or more crystal forms among the same compound is called as polymorphism, and the individual crystals is called as polymorphs each other. The difference in crystal forms sometimes gives rise to a variation in physicochemical properties such as density, melting point, solubility and stability.

It is therefore useful to study the polymorphism of a candidate pharmaceutical compound and to obtain the compound in a single crystal form that exhibits excellent physicochemical properties. However, it is not easy to find out a single crystal form and a method for supplying such a crystal form. Further, it needs to evaluate the properties of a single crystal found and to conduct intensive study.

Patent Document 1 describes arylalkylamine compounds useful for the prevention or treatment of diseases such as hyperparathyroidism. As an example, there is described a dihydrochloride salt of 4-(3S-(1R-(1-naphthyl)ethylamino)pyrrolidin-1-yl)phenylacetic acid (hereinafter, also written as Compound (A)) represented by the formula below.

[Chem. 1]

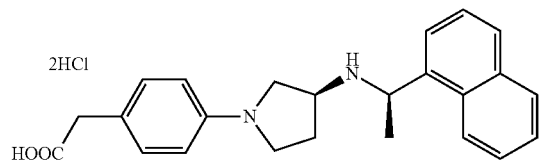

However, Patent Document 1 does not describe or suggest the solid state, physicochemical properties or polymorphism of the dihydrochloride salt of Compound (A) (Compound (A')).

Further, Patent Document 1 describes that the dihydrochloride salt of Compound (A) (Compound (A')) may be produced as follows:

[Chem. 2]

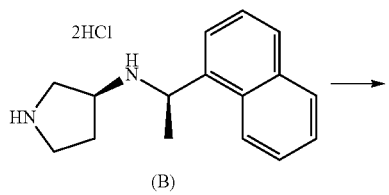

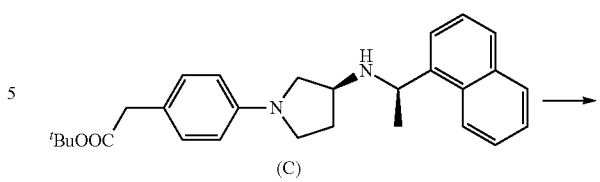

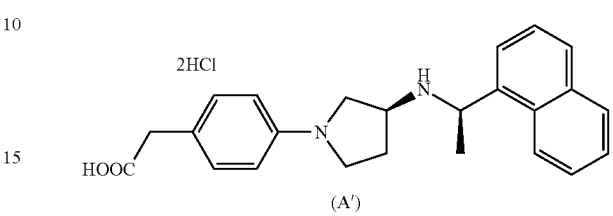

According to Patent Document 1, Compound (B) is produced as follows:

[Chem. 3]

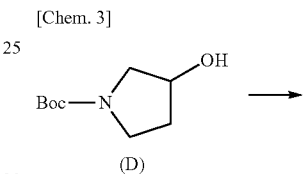

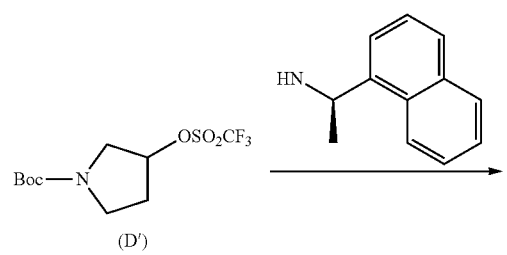

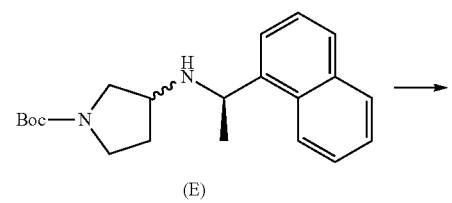

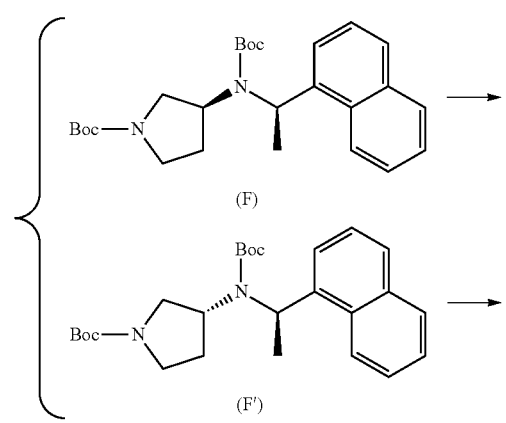

-continued

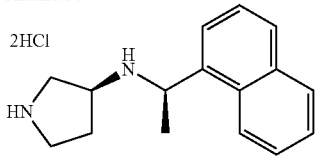

(B)

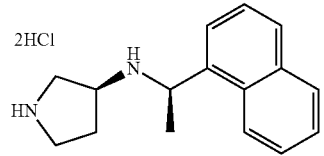

(B')

PRIOR ART DOCUMENT

Patent Document

Patent Document 1: WO 2005/115975

DISCLOSURE OF INVENTION

Problem to be Solved by Invention

An object of the invention is to provide novel crystalline arylalkylamine compounds used for the prevention or treatment of diseases such as hyperparathyroidism, and industrially advantageous processes for producing same compounds.

Means for Solving Problem

After extensive studies directed to solution of the above problem, the present inventors have found that the dihydrochloride salt of Compound (A) described in Patent Document 1 is produced in an amorphous form and the stability of the salt of Compound (A) needs to be studied. The present inventors then studied the properties and stability of the forms of Compound (A) and various salts thereof from various aspects. As a result, the present inventors have found that free form of Compound (A) is preferable as a form of active pharmaceutical ingredient, and have also found that free form of Compound (A) exists in two crystal forms. It has been further found that these two forms of crystals have good storage stability and in particular the form A crystal is most thermodynamically stable.

Compound (E) described in Patent Document 1 is produced as a mixture of diastereomers, and each isomer could not be separated easily even by column purification. Due to these facts, the production of Compound (B) involves the conversion of Compound (E) into Compound (F) and Compound (F'), followed by the separation of the diastereomers by complicated column purification. The many steps and the need of column chromatography make the production process described in Patent Document 1 less attractive on an industrial scale.

The present inventors then conducted various studies in order to develop an industrially advantageous production process. As a result, the present inventors have found that objective Compound (B) may be produced in a high yield by virtue of good stereoselectivity and/or high purity realized by (1) using optically active Compound (D), (2) protecting the hydroxyl group of Compound (D) with a 2-nitrobenzenesulfonyl group rather than with such a protective group as a trifluoromethanesulfonyl group or a methanesulfonyl group, and (3) using a specific base in the reaction. The present invention has been completed based on the findings.

A summary of the present invention is as follows.

1. A crystal of 4-(3S-(1R-(1-naphthyl)ethylamino)pyrrolidin-1-yl)phenylacetic acid.

2. A form A crystal of 4-(3S-(1R-(1-naphthyl)ethylamino)pyrrolidin-1-yl)phenylacetic acid showing peaks at 17.3°±0.2° and 22.6°±0.2° as diffraction angles expressed as 2θ in the powder X-ray diffraction spectrum.

3. A form A crystal of 4-(3S-(1R-(1-naphthyl)ethylamino)pyrrolidin-1-yl)phenylacetic acid showing peaks at 14.6°±0.2°, 14.8°±0.2°, 17.3°±0.2°, 22.6°±0.2° and 24.5°±0.2° as diffraction angles expressed as 2θ in the powder X-ray diffraction spectrum.

4. A form A crystal of 4-(3S-(1R-(1-naphthyl)ethylamino)pyrrolidin-1-yl)phenylacetic acid showing peaks at 12.7°±0.2°, 14.6°±0.2°, 14.8°±0.2°, 17.3°±0.2°, 18.6°±0.2°, 19.1°±0.2°, 20.5°±0.2°, 22.6°±0.2°, 24.5°±0.2° and 28.1°±0.2° as diffraction angles expressed as 2θ in the powder X-ray diffraction spectrum.

5. A form A crystal of 4-(3S-(1R-(1-naphthyl)ethylamino)pyrrolidin-1-yl)phenylacetic acid of which a powder X-ray diffraction spectrum has a pattern illustrated in FIG. 1.

6. A form A crystal of 4-(3S-(1R-(1-naphthyl)ethylamino)pyrrolidin-1-yl)phenylacetic acid having a melting point of 174 to 177° C. as measured by differential scanning calorimetry.

7. A form B crystal of 4-(3S-(1R-(1-naphthyl)ethylamino)pyrrolidin-1-yl)phenylacetic acid showing peaks at 15.9°±0.2° and 21.4°±0.2° as diffraction angles expressed as 2θ in the powder X-ray diffraction spectrum.

8. A form B crystal of 4-(3S-(1R-(1-naphthyl)ethylamino)pyrrolidin-1-yl)phenylacetic acid showing peaks at 15.9°±0.2°, 19.7°±0.2°, 21.4°±0.2°, 23.8°±0.2° and 24.3°±0.2° as diffraction angles expressed as 2θ in the powder X-ray diffraction spectrum.

9. A form B crystal of 4-(3S-(1R-(1-naphthyl)ethylamino)pyrrolidin-1-yl)phenylacetic acid showing peaks at 12.6°±0.2°, 14.4°±0.2°, 15.9°±0.2°, 18.6°±0.2°, 19.1°±0.2°, 19.7°±0.2°, 21.4°±0.2°, 23.8°±0.2°, 24.3°±0.2° and 28.0°±0.2° as diffraction angles expressed as 2θ in the powder X-ray diffraction spectrum.

10. A form B crystal of 4-(3S-(1R-(1-naphthyl)ethylamino)pyrrolidin-1-yl)phenylacetic acid of which a powder X-ray diffraction spectrum has a pattern illustrated in FIG. 3.

11. A form B crystal of 4-(3S-(1R-(1-naphthyl)ethylamino)pyrrolidin-1-yl)phenylacetic acid having a melting point of 164 to 167° C. as measured by differential scanning calorimetry.

12. A medicine comprising the crystal described in any of the above 1 to 11.

13. A pharmaceutical composition comprising the crystal described in any of the above 1 to 11, and a pharmacologically acceptable carrier.

14. A CaSR agonist comprising the crystal described in any of the above 1 to 11.

15. A drug for the prevention or treatment of hyperparathyroidism comprising the crystal described in any of the above 1 to 11.

16. A process for producing a form A crystal of 4-(3S-(1R-(1-naphthyl)ethylamino)pyrrolidin-1-yl)phenylacetic acid, comprising crystallizing 4-(3S-(1R-(1-naphthyl)ethylamino)pyrrolidin-1-yl)phenylacetic acid in an appropriate solvent in the presence of a base by adding an acid at 50 to 70° C.

17. A process for producing a form B crystal of 4-(3S-(1R-(1-naphthyl)ethylamino)pyrrolidin-1-yl)phenylacetic acid, comprising rapidly crystallizing 4-(3S-(1R-(1-naphthyl)ethylamino)pyrrolidin-1-yl)phenylacetic acid in an appropriate solvent in the presence of a base by adding an acid at 20 to 40° C.

18. A process for producing a form A crystal of 4-(3S-(1R-(1-naphthyl)ethylamino)pyrrolidin-1-yl)phenylacetic acid, comprising seeding a form A crystal to a slurry of a form B crystal of 4-(3S-(1R-(1-naphthyl)ethylamino)pyrrolidin-1-yl)phenylacetic acid and crystallizing the form A crystal at 40 to 70° C., or dissolving a form B crystal into a solution comprising a good solvent and a poor solvent at 40 to 60° C. and then recrystallizing the form A crystal at 20 to 25° C.

19. A process for producing a compound represented by Formula (4):

[Chem. 7]

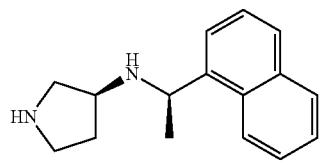
(4)

or a salt thereof
comprising:
reacting a compound represented by Formula (1):

[Chem. 4]

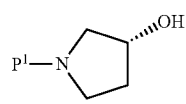
(1)

(wherein $P^1$ is an amino-protecting group)
with a 2-nitrobenzenesulfonyl halide to form a compound represented by Formula (2):

[Chem. 5]

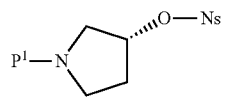
(2)

(wherein Ns is 2-nitrobenzenesulfonyl and $P^1$ is the same as defined above);

reacting the compound with 1R-(1-naphthyl)ethylamine in the presence of a base to form a compound represented by Formula (3):

[Chem. 6]

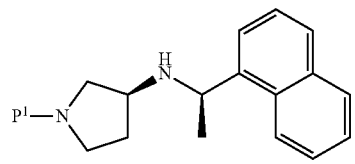
(3)

(wherein $P^1$ is the same as defined above); and
deprotecting the compound.

20. A process for producing a crystal of a compound represented by Formula (7):

[Chem. 11]

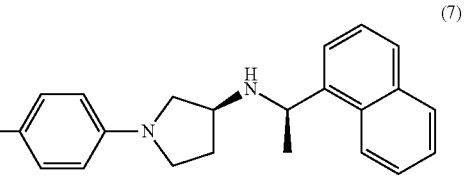
(7)

comprising:
reacting a compound represented by Formula (4):

[Chem. 8]

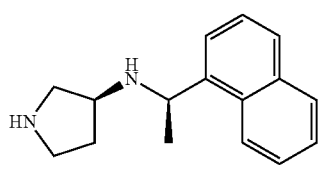
(4)

or a salt thereof, after it is treated with a base as necessary, with a compound represented by Formula (5):

[Chem. 9]

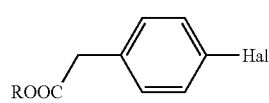
(5)

(wherein Hal is a halogen and R is a carboxylic acid-protecting group)
in the presence of a palladium catalyst, a base and a ligand to form a compound represented by Formula (6):

[Chem. 10]

(6)

ROOC—⟨phenyl⟩—N(pyrrolidine)—NH—CH(CH₃)—naphthyl (wherein R is the same as defined above)
or a salt thereof; and hydrolyzing the compound or the salt with a base followed by neutralization with an acid.

21. A process for producing a crystal of a compound represented by Formula (7):

[Chem. 18]

(7)

HOOC—⟨phenyl⟩—N(pyrrolidine)—NH—CH(CH₃)—naphthyl comprising:

reacting a compound represented by Formula (1):

[Chem. 12]

(1)

P¹—N(pyrrolidine)—OH (wherein P¹ is an amino-protecting group)
with a 2-nitrobenzenesulfonyl halide to form a compound represented by Formula (2):

[Chem. 13]

(2)

P¹—N(pyrrolidine)—O—Ns (wherein Ns is 2-nitrobenzenesulfonyl and P¹ is the same as defined above);

reacting the compound with 1R-(1-naphthyl)ethylamine in the presence of a base to form a compound represented by Formula (3):

[Chem. 14]

(3)

P¹—N(pyrrolidine)—NH—CH(CH₃)—naphthyl (wherein P¹ is the same as defined above);

deprotecting the compound to form a compound represented by Formula (4):

[Chem. 15]

(4)

HN(pyrrolidine)—NH—CH(CH₃)—naphthyl or a salt thereof reacting the compound or the salt, after it is treated with a base as necessary, with a compound represented by Formula (5):

[Chem. 16]

(5)

ROOC—⟨phenyl⟩—Hal (wherein Hal is a halogen and R is a carboxylic acid-protecting group)

in the presence of a palladium catalyst, a base and a ligand to form a compound represented by Formula (6):

[Chem. 17]

(6)

ROOC—⟨phenyl⟩—N(pyrrolidine)—NH—CH(CH₃)—naphthyl (wherein R is the same as defined above)
or a salt thereof; and hydrolyzing the compound or the salt with a base followed by neutralization with an acid.

22. A compound represented by Formula (6):

[Chem. 19]

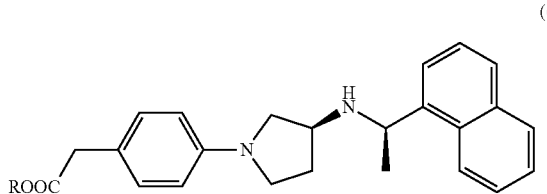

(6)

(wherein R is a carboxylic acid-protecting group) or a salt thereof.

23. The compound or the salt thereof described in 22, wherein R is ethyl.

Effects of Invention

The crystals (the form A crystal and the form B crystal) of Compound (A) according to the present invention are novel and highly stable. In particular, the inventive crystals of Compound (A) may be stored under constant conditions with little occurrence of related substance. By virtue of such excellent storage stability, the crystals are preferable as pharmaceutical ingredients.

The inventive processes for the production of crystals of Compound (A) are industrially advantageous processes capable of producing pharmaceutically useful Compound (A) in good yield and through short step.

BEST MODE FOR CARRYING OUT INVENTION

The substituent represented by each symbol in the specification indicates the following meaning.

As an "amino-protecting group" in P¹, there is mentioned the amino-protecting group usually used in the field of organic synthetic chemistry, for example, t-butoxycarbonyl, benzyloxycarbonyl and p-methoxybenzyl, etc., with t-butoxycarbonyl being particularly preferable.

As a "halogen" in Hal, there are mentioned fluorine atom, chlorine atom, bromine atom or iodine atom, etc.

As a "carboxylic acid-protecting group" in R, there is an alkyl, a substituted alkyl or tetrahydropyranyl, etc. Examples of the alkyls include linear or branched alkyls having 1 to 4 carbon atoms such as methyl, ethyl, propyl, isopropyl, butyl and tertiary butyl. Examples of the substituted alkyls include the above alkyls substituted with such substituents as alkoxyls and phenyls, with specific examples including methoxymethyl, methoxyethoxymethyl, benzyloxymethyl, benzyl and triphenylmethyl. The "carboxylic acid-protecting group" in R is preferably an alkyl, and particularly preferably ethyl.

The form A crystal of Compound (A) of the present invention is characterized by one or more of the following features.

Figure 1:
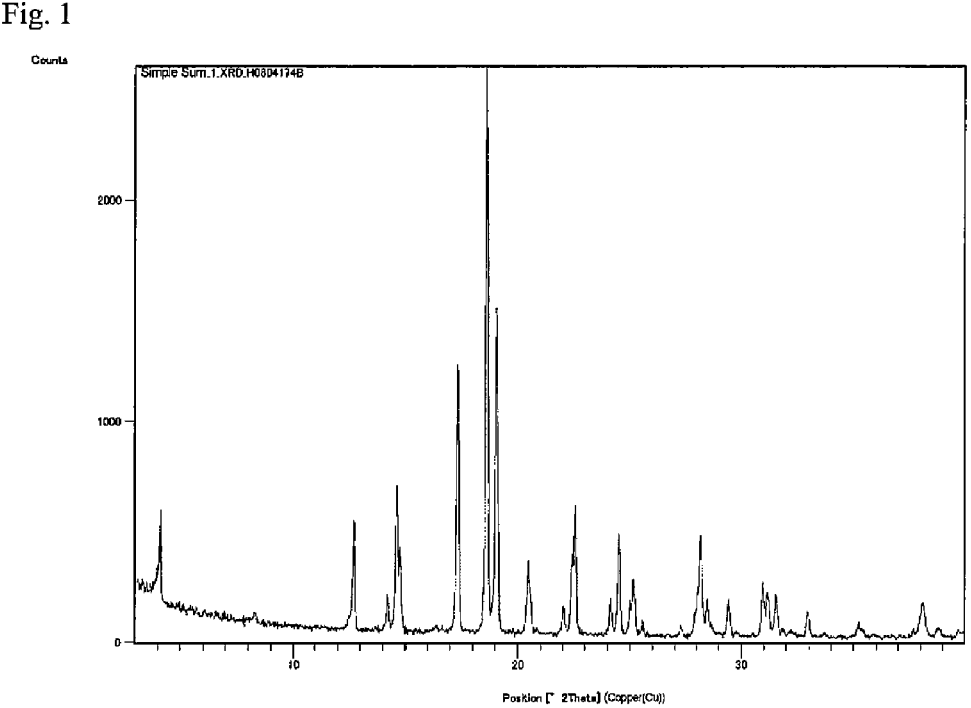
FIG. 1 shows a powder X-ray diffraction pattern of a form A crystal of Compound (A).
Figure 2:
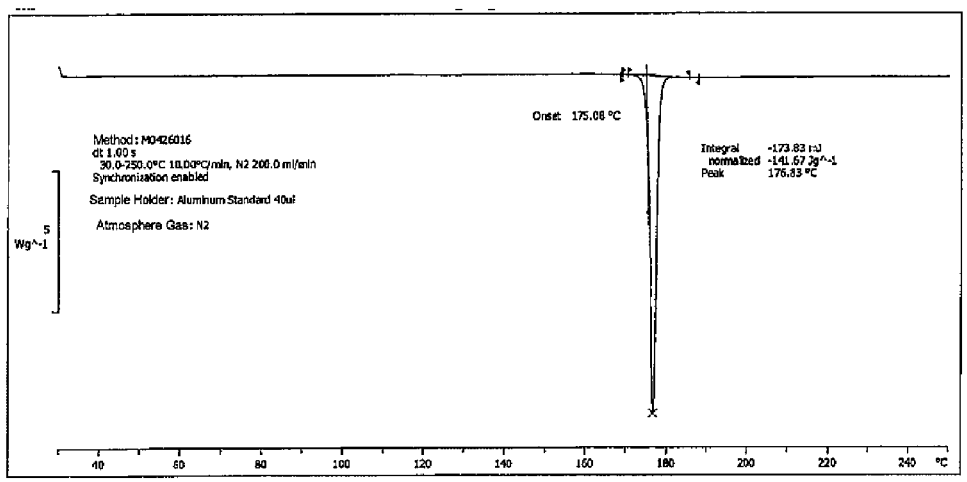
FIG. 2 shows a DSC curve of a form A crystal of Compound (A).

(1) The crystal preferably has a powder X-ray diffraction pattern illustrated in FIG. 1 and/or a differential scanning calorimetry (DSC) curve illustrated in FIG. 2.

(2) In a powder X-ray diffraction pattern, the form A crystal may have characteristic peaks at 17.3°±0.2° and 22.6°±0.2° as diffraction angles expressed as 2θ. Other characteristic peaks may include those appearing at 14.6°±0.2°, 14.8°±0.2° and 24.5°±0.2°, and further may include those appearing at 12.7°±0.2°, 18.6°±0.2°, 19.1°±0.2°, 20.5°±0.2° and 28.1°±0.2°.

(3) The DSC melting point (the extrapolated onset temperature) is 174 to 177° C., and is in particular around 175° C.

The form B crystal of Compound (A) of the present invention is characterized by one or more of the following features.

Figure 3:
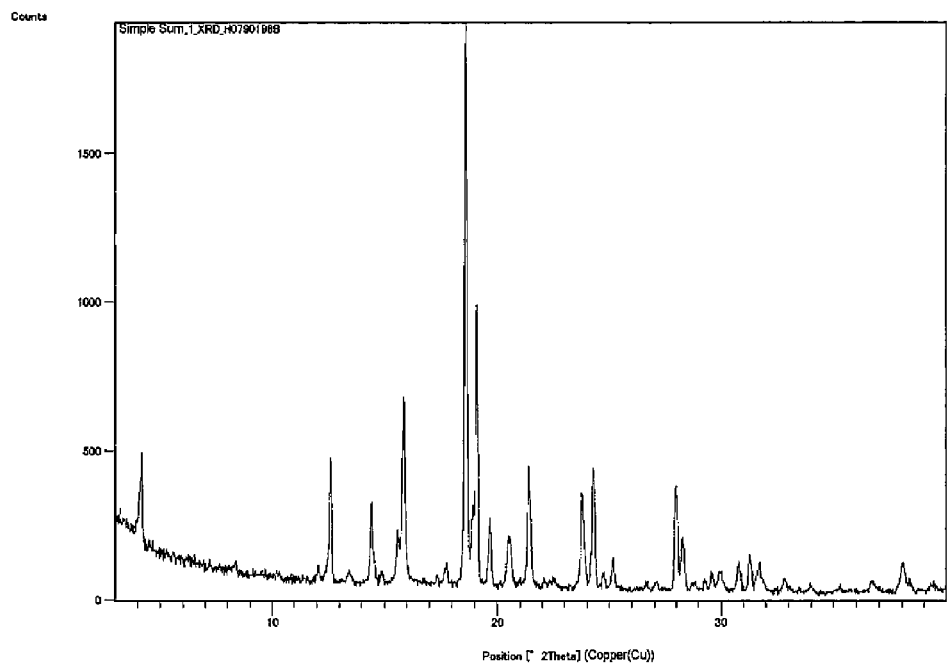
FIG. 3 shows a powder X-ray diffraction pattern of a form B crystal of Compound (A).
Figure 4:
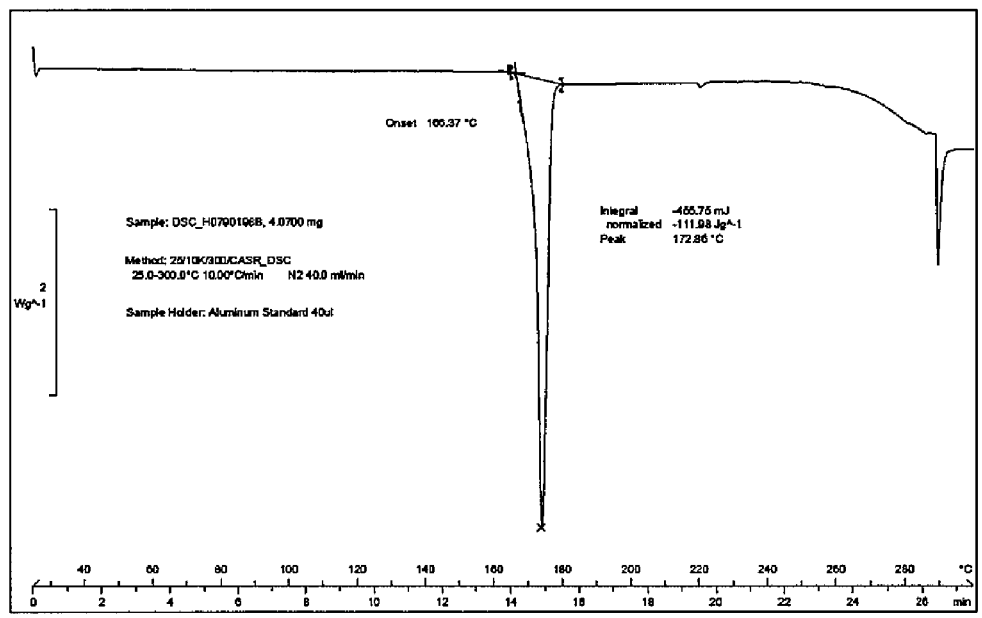
FIG. 4 shows a DSC curve of a form B crystal of Compound (A).

(1) The crystal preferably has a powder X-ray diffraction pattern illustrated in FIG. 3 and/or a DSC curve illustrated in FIG. 4.

(2) In a powder X-ray diffraction pattern, the form B crystal may have characteristic peaks at 15.9°±0.2° and 21.4°±0.2° as diffraction angles expressed as 2θ. Other characteristic peaks may include those appearing at 19.7°±0.2°, 23.8°±0.2° and 24.3°±0.2°, and further may include those appearing at 12.6°±0.2°, 14.4°±0.2°, 18.6°±0.2°, 19.1°±0.2° and 28.0°±0.2°.

(3) The DSC melting point (the extrapolated onset temperature) is 164 to 167° C., and is in particular around 166° C.

Compound (A) of the present invention may be produced as illustrated below.

[Chem. 20]

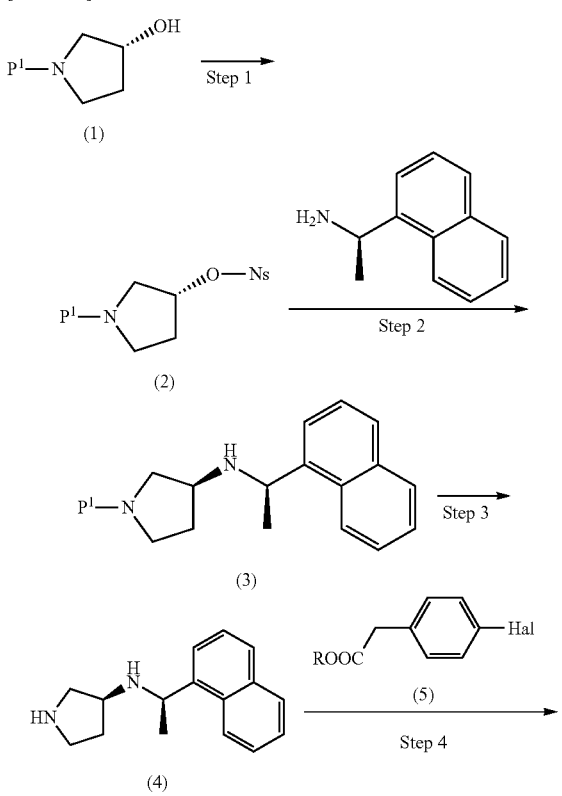

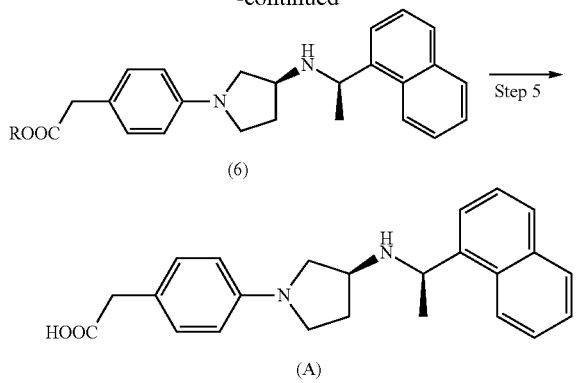

(In the formulae, $P^1$ is an amino-protecting group such as t-butoxycarbonyl, Ns is 2-nitrobenzenesulfonyl group, Hal is a halogen such as chlorine atom or bromine atom, and R is a carboxylic acid-protecting group such as an alkyl having 1 to 4 carbon atoms (for example, ethyl).)

Step 1:

The reaction for introducing 2-Nitrobenzenesulfonyl group onto the hydroxyl group in Compound (1) may be performed in accordance with the method described in Theodora W. Greene, Peter G. M. Wuts, "Protective Groups in Organic Synthesis" 4th. ed., John Wiley & Sons, Inc., 2007. For example, Compound (1) and a 2-nitrobenzenesulfonyl halide may be reacted with each other in a solvent in the presence of a base.

Examples of the 2-nitrobenzenesulfonyl halides include 2-nitrobenzenesulfonyl chloride and 2-nitrobenzenesulfonyl bromide, with 2-nitrobenzenesulfonyl chloride being preferable.

The solvent is not limited as long as it does not affect the reaction. Examples of the solvents include aromatic hydrocarbons (such as benzene, toluene and xylene), aprotic polar solvents (such as N,N-dimethylformamide, N,N-dimethylacetamide and dimethylsulfoxide), nitriles (such as acetonitrile), ketones (such as acetone and methyl ethyl ketone), esters (such as ethyl acetate) and ethers (such as diethyl ether and tetrahydrofuran). Of these, nitriles are preferable, and acetonitrile is particularly preferable.

Examples of the bases include triethylamine, diisopropylethylamine and 1,8-diazabicyclo[5.4.0]undec-7-ene (DBU). Of these, triethylamine is preferable.

2-Nitrobenzenesulfonyl halide is used in 1.0 to 1.5 equivalents, and preferably 1.0 to 1.1 equivalents relative to Compound (1). The base is used in 1.0 to 1.5 equivalents, and preferably 1.0 to 1.3 equivalents relative to Compound (1). The solvent is used in a ratio to Compound (1) of 2 to 5 w/w, and preferably 2 to 3.5 w/w. The reaction may be performed at 0° C. to room temperature.

Step 2:

The reaction of Compound (2) and 1R-(1-naphthyl)ethylamine may be performed in a solvent in the presence of a base.

The solvent is not limited as long as it does not affect the reaction. Examples of the solvents include aromatic hydrocarbons (such as benzene, toluene and xylene), aprotic polar solvents (such as N,N-dimethylformamide, N,N-dimethylacetamide and dimethylsulfoxide), nitriles (such as acetonitrile), ketones (such as acetone and methyl ethyl ketone), esters (such as ethyl acetate) and ethers (such as diethyl ether and tetrahydrofuran). Of these, nitriles are preferable, and acetonitrile is particularly preferable.

Examples of the bases include inorganic bases (such as sodium hydrogencarbonate, sodium carbonate, potassium carbonate and tripotassium phosphate), and organic bases (such as triethylamine, diisopropylethylamine and N-methylmorpholine). Preferred bases include potassium carbonate, tripotassium phosphate and diisopropylethylamine, with tripotassium phosphate being particularly preferable.

1R-(1-Naphthyl)ethylamine is used in 1.1 to 1.3 equivalents, and preferably 1.2 equivalents relative to Compound (1). The base is usually used in 0.5 to 2 equivalents. Tripotassium phosphate is used in 0.5 to 1.5 equivalents, and preferably 0.7 equivalents.

The solvent is used in a ratio of 2 to 3 w/w, and preferably 2.2 to 2.4 w/w.

The reaction may be performed at 50 to 100° C., and preferably 70 to 80° C.

Step 3:

The deprotection reaction of Compound (3) may be performed, for example, in a solvent in the presence of an acid in accordance with the method described in Theodora W. Greene, Peter G. M. Wuts, "Protective Groups in Organic Synthesis" 4th. ed., John Wiley & Sons, Inc., 2007.

Examples of the solvents include alcohols (such as methanol, ethanol and isopropanol) and ethers (such as diethyl ether and tetrahydrofuran). Of these, alcohols are preferable, and isopropanol is particularly preferable.

Examples of the acids include trifluoroacetic acid, hydrochloric acid, methanesulfonic acid, acetyl chloride, propionyl chloride and trimethylsilyl chloride, with acetyl chloride being particularly preferable.

The acid is used in 2 to 5 equivalents, and preferably 3 to 4 equivalents relative to Compound (3). The solvent is used in a ratio to Compound (3) of 3 to 10 w/w, and preferably 5 to 7 w/w. The reaction may be performed at 0 to 100° C., and preferably 50 to 70° C.

Step 4:

The reaction of Compound (4) and Compound (5) may be performed in a solvent in the presence of a palladium catalyst, a base and a ligand.

The solvent is not limited as long as it does not affect the reaction. Examples of the solvents include aromatic hydrocarbons (such as benzene, toluene and xylene), aprotic polar solvents (such as N,N-dimethylformamide and dimethylsulfoxide), ethers (such as diethyl ether and 1,4-dioxane), alcohols (such as 1-butanol), nitriles (such as acetonitrile), and mixtures of these solvents.

Examples of the palladium catalysts include palladium chloride, palladium acetate, dichloro[1,1'-bis(diphenylphosphino)ferrocene]palladium ($PdCl_2(dppf)$) and tetrakistriphenylphosphinepalladium.

Examples of the bases include alkali metal lower alkoxides (such as sodium t-butoxide) and inorganic bases (such as cesium carbonate, potassium carbonate and sodium carbonate).

Examples of the ligands include 1,1'-bis(diphenylphosphino)ferrocene, 2-dicyclohexylphosphino-2',6'-dimethoxybiphenyl (S-PHOS), 2-dicyclohexylphosphino-2',4',6'-triisopropylbiphenyl (X-PHOS) and 4,5-bis(diphenylphosphino)-9,9-dimethylxanthene (Xantphos).

Compound (5) is used in 1.0 to 2.0 equivalents, and preferably 1.1 to 1.5 equivalents relative to Compound (4). The palladium catalyst is used in 0.005 to 1 equivalent, and preferably 0.01 to 0.2 equivalents relative to Compound (4). The ligand is used in 0.005 to 1 equivalent, and preferably 0.01 to 0.2 equivalents relative to Compound (4). The base is used in 0.5 to 5 equivalents, and preferably 2.5 to 3.5 equivalents relative to Compound (4).

The reaction is performed at 25 to 150° C., and preferably 80 to 120° C. The reaction time is variable depending on the reaction conditions, but is usually 10 minutes to 12 hours, and preferably 30 minutes to 8 hours.

When Compound (4) is in the form of, for example, a salt (hydrochloride salt) or a hydrate, such Compound (4) may be treated with a base by a common method, followed by reacting with Compound (5). Examples of the bases include sodium hydroxide and potassium hydroxide.

Compound (6) obtained, and Compound (6) wherein R is preferably ethyl is a novel compound. As a salt of Compound (6), the hydrochloride salt is preferable.

Step 5:

The hydrolysis reaction of Compound (6) may be performed by treating the compound with a base in a solvent in accordance with a common method.

Examples of the solvents include alcohols (such as methanol, ethanol and isopropanol) and water.

Examples of the bases include inorganic bases (such as sodium hydroxide, potassium hydroxide, sodium hydrogencarbonate, potassium hydrogencarbonate, sodium carbonate and potassium carbonate) and organic bases (such as triethylamine, diisopropylethylamine, 1,8-diazabicyclo[5.4.0]undec-7-ene (DBU) and pyridine). In particular, inorganic bases are preferable, and sodium hydroxide is particularly preferable.

The reaction may be performed at 0 to 100° C.

The compound resulting from the hydrolysis reaction is neutralized with an acid to give Compound (A).

Examples of the acids used for the neutralization include weak acids such as inorganic acids (such as carbonic acid and boric acid) and organic acids (such as acetic acid and citric acid). In particular, organic acids are preferable, and citric acid is particularly preferable.

Examples of the solvents include alcohols (such as methanol, ethanol and isopropanol) and water.

When the reaction solution of Compound (A) obtained by the hydrolysis reaction in this step is neutralized with an acid at a temperature condition of 50 to 70° C., Compound (A) may be obtained as the form A crystal. The form A crystal may be formed efficiently by acid-treating the solution at the above reaction temperature for 1 to 10 hours, preferably 1 to 3 hours, and then cooling the solution slowly from 10° C. to room temperature.

Compound (A) may be obtained as the form B crystal by rapidly neutralizing the reaction solution of Compound (A) with an acid at a temperature of 20 to 40° C. The form B crystal may be formed efficiently by filtering off the crystal soon at the above reaction temperature, preferably after the crystal is precipitated by the addition of the acid. The time between the addition of the acid and the filtration of the form B crystal is variable depending on the reaction scale, but is usually 10 seconds to 3 minutes, and preferably 30 seconds to 1 minute.

The form B crystal of Compound (A) may be transformed into the form A crystal by seeding the form A crystal to a slurry of the form B crystal in an alcohol (such as methanol, ethanol or isopropanol) or to a slurry of the form B crystal resulting from the acid neutralization in the above step 5, followed by stirring. The stirring temperature is usually 40 to 70° C., and preferably 40 to 60° C. The stirring time depends on variables such as reaction scale and stirring temperature, but is usually 1 hour to 3 days, and preferably 3 hours to 63 hours.

Alternatively, the form B crystal of Compound (A) may be transformed into the form A crystal by dissolving the form B crystal with a good solvent (such as dimethylsulfoxide or dimethylacetamide) and a poor solvent (such as an alcohol (such as methanol, ethanol or isopropanol), acetone, toluene, methyl t-butyl ether, methyl ethyl ketone, methyl isobutyl ketone, acetonitrile, ethyl acetate or water), followed by recrystallization. The dissolution temperature is 40 to 60° C., and preferably 55° C. The temperature condition during the recrystallization is 20 to 25° C. The mixing ratio (the volume ratio) of the good solvent to the poor solvent is preferably 1:1 to 1:3.

In each reaction, a treatment after the reaction may be performed by common methods. To isolate and purify the compound, common methods such as crystallization, distillation and liquid separation may be selected appropriately or may be performed in any combination. The crystallization method in the present invention may be any known method. In particular, an industrially advantageous method is desirable. For example, recrystallization is preferable.

According to the production process of the present invention, Compound (A) may be obtained in a single crystal form as the form A crystal or the form B crystal. Further, in some cases, Compound (A) is obtained as a mixture. Here, the mixture means a mixture containing 1% or more of one or more other types of crystal forms. The mixture proportion in the mixture may be arbitrary. In the present invention, the crystal preferably has a single crystal form.

The inventive crystal of Compound (A) obtained as described above is so stable that quantity synthesis of the compound becomes feasible and the compound is easily produced into preparations such as tablets. For these reasons, the crystal itself is useful as a pharmaceutical ingredient. Further, a mixture of the crystal forms of the present invention may be used as a pharmaceutical ingredient.

As will be described later in Reference Examples 2 and 3, the previously known dihydrochloride salt of Compound (A) is produced as an amorphous product including a pharmaceutically unacceptable solvent, and it is difficult to obtain the salt in the form of a crystal with stable chemical equivalents of the hydrochloric acid and the solvent. In contrast, crystals of free Compound (A) and of the monohydrochloride thereof and of the monohydrobromide thereof may be obtained with stable chemical equivalents of the acid and a solvent. In particular, the form A crystal and the form B crystal of Compound (A) of the present invention have good storage stability. In particular, the form A crystal of Compound (A) is more thermodynamically stable than the form B crystal. By virtue of these characteristics, the form A and form B crystals of Compound (A) of the present invention may provide high-quality pharmaceutical ingredients.

The inventive form A and form B crystals of Compound (A) obtained as described above are useful for the prevention or treatment of various diseases that are expected to be pathologically improved by the activation of CaSR and/or the suppression of PTH production (and/or the reduction of in-blood PTH level by any of the above approaches). Examples of such diseases include hyperparathyroidism (such as primary hyperparathyroidism, secondary hyperparathyroidism and ectopic hyperparathyroidism).

For pharmaceutical uses, the inventive crystals of Compound (A) as active ingredients may be formulated together with inert carriers selected in accordance with the mode of administration into common pharmaceutical preparations (such as tablets, granules, capsules, powders, solutions, suspensions, emulsions, injections and drops). Examples of such carriers include general pharmaceutically acceptable binders (such as gum arabic, gelatin, sorbitol and polyvinylpyrrolidone), excipients (such as lactose, sugar, cornstarch and sorbitol), lubricants (such as magnesium stearate, talc and polyethylene glycol) and disintegrants (such as potato starch). The crystals may be formulated into injections and drops with use of distilled water for injection, physiological saline or aqueous glucose solution, etc.

In pharmaceutical uses, the inventive crystals of Compound (A) may be administered by any methods without limitation. Any of general oral or parenteral administration methods (such as intravenous administration, intramuscular administration, subcutaneous administration, transdermal administration, nasal administration, other transmucosal administration and enteral administration) may be applicable.

In pharmaceutical uses, the inventive crystals of Compound (A) may be administered in amounts determined appropriately in accordance with the potency and characteristics of the active ingredient compound while ensuring that the medicinal effects are obtained sufficiently. The dose is variable in accordance with the mode of administration and the patient age, body weight and condition, and is selected in the general range, for example, 0.001 to 300 mg/kg per day.

EXAMPLES

Hereinbelow, the present invention will be described in detail based on Examples, Reference Examples and Experiment Examples without limiting the scope of the invention by such examples.

Example 1

Production of 4-(3S-(1R-(1-naphthyl)ethylamino) pyrrolidin-1-yl)phenylacetic Acid (Form A Crystal)

(1)

[Chem. 21]

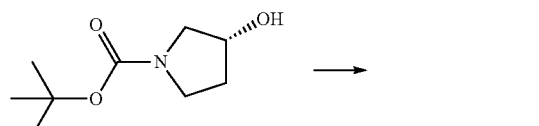

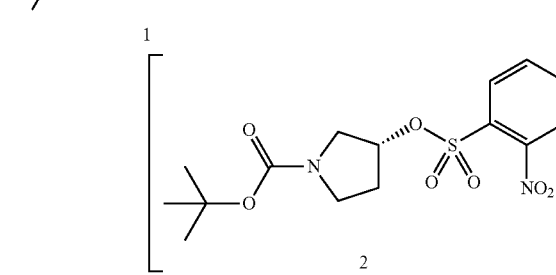

Compound 1 (25.0 g), trimethylamine hydrochloride (2.33 g), acetonitrile (81.0 g) and triethylamine (17.2 g) were mixed together, and the mixture was cooled to 5° C. To the mixture, a 25% toluene solution (125 g) of 2-nitrobenzenesulfonyl chloride was added dropwise, and the remaining toluene solution was added by washing with acetonitrile (8.53 g). The reaction solution was reacted at 7° C. for 2 hours. After the reaction, water (27.0 g) was added. Thereafter, a mixture of water (43.5 g) and concentrated hydrochloric acid (5.05 g) was added dropwise. The solution was raised to room temperature and was separated. Water (80.8 g) was added to the organic phase and the mixture was separated. The same operation was performed again. The organic phase was concentrated to give a toluene solution (108 ml) of Compound 2. The solution was subjected to the next step without isolating the compound.

(2)

[Chem. 22]

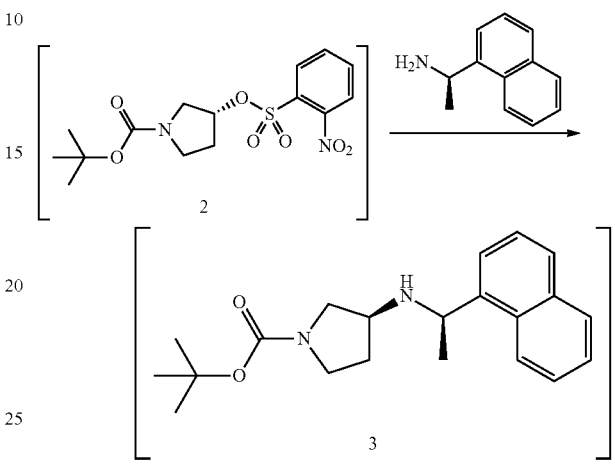

The toluene solution (54 ml) of Compound 2, 1R-(1-naphthyl)ethylamine (13.7 g), tripotassium phosphate (9.92 g) and acetonitrile (29.6 g) were mixed together, and the mixture was reacted at 70 to 75° C. for 20 hours. The reaction solution was cooled to 50° C., and water (100 g) and ethyl acetate (33.8 g) were added. The mixture was stirred for 10 minutes and was thereafter separated. The organic phase was cooled to room temperature, and then water (50.0 g) and tripotassium phosphate (2.83 g) were added. The resultant mixture was stirred and was separated. Water (50.0 g) was added to the organic phase, and the mixture was stirred and was separated. The organic phase was concentrated to give a concentrated residue (51.5 ml) of Compound 3. The residue was subjected to the next step.

(3)

[Chem. 23]

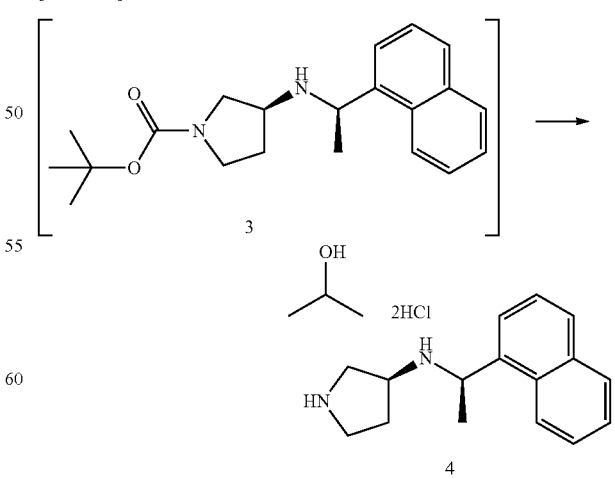

Isopropanol (79.1 g) was cooled to 5° C., and acetyl chloride (18.9 g) was added thereto dropwise, and the remaining acetyl chloride was added by washing with isopropanol (5.29 g). The mixture was reacted at 0 to 10° C. for 30 minutes. Thereafter, a mixture of the concentrated residue (51.5 ml) of Compound 3 and isopropanol (30.0 g) was added dropwise, and the remaining mixture was added by washing with isopropanol (12.3 g). The reaction solution was heated to 55 to 60° C., and was reacted for 2 hours. In case that any crystal was not precipitated in the reaction solution after the reaction, a seed crystal (12.5 mg) of Compound 4 was added and the mixture was stirred at the same temperature for 1 hour. The reaction solution was cooled to room temperature in 2 hours and was thereafter stirred for 3 hours. The crystal of Compound 4 was filtered off and then washed with isopropanol (15.8 g). The crystal obtained was dried to give a white crystal of Compound 4 (18.44 g, yield 74.0%).

MS•APCI (m/z): 241 [M+H]$^+$ (4)

[Chem. 24]

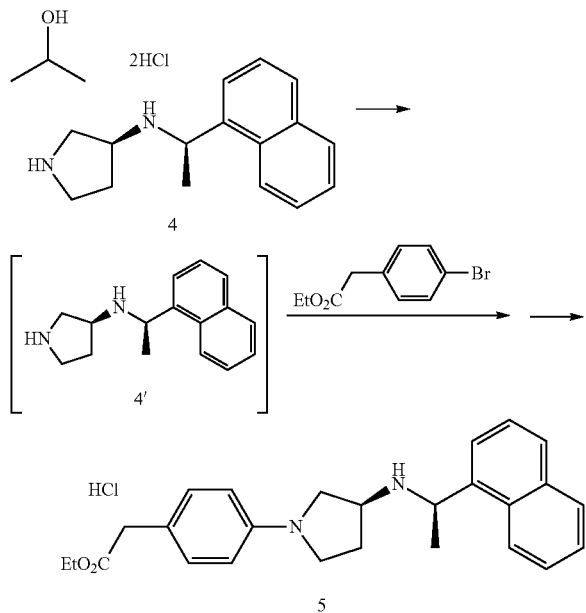

Toluene (1130 g), a 4 M aqueous sodium hydroxide solution (598 g) and Compound 4 (260 g) were mixed together, and the mixture was stirred at room temperature for 30 minutes and separated. The organic phase was concentrated to a volume of 1 L, and toluene (22 g) was added. A toluene (90.0 g) solution of cesium carbonate (681 g), palladium (II) acetate (3.1 g), 2-dicyclohexylphosphino-2', 4',6'-triisopropylbiphenyl (X-phos, 7.3 g), water (3.4 g) and ethyl 4-bromophenylacetate (203 g) was added, and the remaining toluene solution was added by washing with toluene (140 g). After nitrogen substitution, the temperature was raised to 95 to 105° C. and the mixture was reacted for 8 hours. The reaction solution was cooled to room temperature. Water (2080 g) was added, and the mixture was stirred for 10 minutes and was thereafter separated. While stirring, a 7% saline solution (1300 g) was added to the organic phase and the mixture was separated. Ethylene diamine (4.2 g) was added to the organic phase, and the mixture was stirred for 2 hours. Precoat filtration was carried out using activated carbon/KYOURYOKU SHIRASAGI (52.0 g), and the residue was washed with toluene (338 g). To the filtrate, a mixture of concentrated hydrochloric acid (72.8 g) and ethanol (268 g) was added, and the remaining mixture was added by washing with t-butyl methyl ether (200 g). Further, t-butyl methyl ether (1740 g) was added dropwise over a period of 1 hour, and the mixture was stirred for 1 hour. The resultant crystal was filtered off, washed with t-butyl methyl ether (1165 g) and dried to give a white crystal of Compound 5 (239 g, yield: 78.0%).

MS•APCI (m/z): 403 [M+1.1]$^+$ (5)

[Chem. 25]

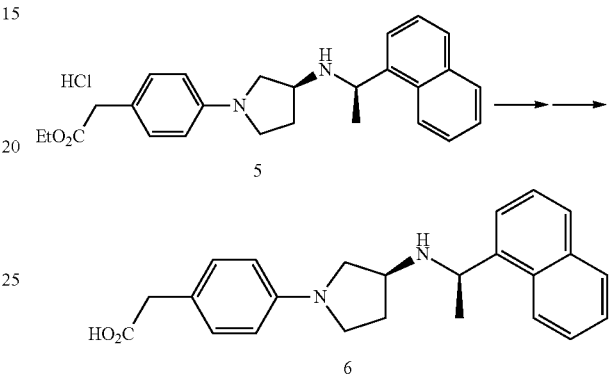

Sodium hydroxide (3.80 g) was added to water (47.4 g). After dissolving, ethanol (39.6 g) was added thereto. While stirring, the mixture was heated to 50° C. and Compound 5 (16.5 g) was added in three portions. The mixture was heated to 60° C., and was reacted for 30 minutes. The reaction solution was filtered and the residue was washed with a mixture of water (11.6 g), sodium hydroxide (0.25 g) and ethanol (9.90 g). At 60° C., a solution of citric acid monohydrate (4.34 g) in water (39.8 g) was added dropwise to the filtrate until a crystal was precipitated. After stirring for 30 minutes, and then the remaining portion of the aqueous citric acid monohydrate solution was added dropwise. After the completion of the dropwise addition, the mixture was stirred for 1 hour and was cooled to 10° C. in 1.5 hours. The pH was adjusted to 7.0 to 9.0, and then the crystal was filtered off. The crystal obtained was washed sequentially with ethanol (19.6 g), water (49.5 g) and ethanol (19.6 g), and was dried to give a white crystal of Compound 6 (12.77 g, yield: 90.7%).

Further, Compound 6 (10.0 g) obtained was added to a solution of sodium hydroxide (1.63 g) in water (33.6 g) and ethanol (28.1 g). The mixture was stirred at 60° C. for 30 minutes. The mixture was filtered, and the residue was washed with a mixture of water (8.20 g), sodium hydroxide (0.18 g) and ethanol (7.00 g). At 60° C., a solution of citric acid monohydrate (3.20 g) in water (29.8 g) was added dropwise to the filtrate until a crystal was precipitated. Thereafter, the mixture was stirred for 30 minutes, and further the remaining portion of the aqueous citric acid monohydrate solution was added dropwise. After the mixture was stirred for 1 hour, the mixture was cooled to 10° C. in 1.5 hours and filtered. The crystal obtained was washed sequentially with ethanol (13.9 g), water (35.2 g) and ethanol (13.9 g), and was thereafter dried to give a form A crystal of Compound 6 (9.58 g, white crystal, yield: 95.8%).

Example 2

Production of 4-(3S-(1R-(1-naphthyl)ethylamino)pyrrolidin-1-yl)phenylacetic Acid (Form B Crystal)

[Chem. 26]

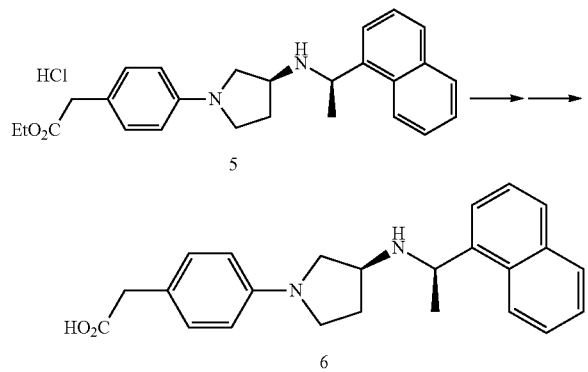

Sodium hydroxide (0.38 g) was added to water (4.74 g). After stirring, ethanol (3.96 g) was added thereto. While stirring, the mixture was heated to 60° C. and Compound 5 (1.65 g) was added in three portions. The mixture was reacted at the same temperature for 30 minutes. The reaction solution was filtered and the residue was washed with a mixture of water (1.16 g), sodium hydroxide (25 mg) and ethanol (0.99 g). The filtrate was cooled to 25° C., and a solution of citric acid monohydrate (434 mg) in water (3.98 g) was added dropwise. The mixture was filtered within 1 minute after the dropwise addition. The crystal obtained was washed sequentially with ethanol (1.96 g), water (4.95 g) and ethanol (1.96 g), and was thereafter dried to give a form B crystal of Compound 6 (1.28 g, white crystal, yield: 90.9%).

Example 3

(Alternative) Production of 4-(3S-(1R-(1-naphthyl)ethylamino)pyrrolidin-1-yl)phenylacetic Acid (Form B Crystal)

Ethanol (30 ml) and water (3 ml) were added to 4-(3S-(1R-(1-naphthyl)ethylamino)pyrrolidin-1-yl)phenylacetic acid (150 mg) to give a suspension. The suspension was heated to dissolve part of the acid and the reaction solution was stirred at room temperature overnight. The powder precipitated was filtered off and was dried by blowing air at 50° C. overnight to give a form B crystal of 4-(3S-(1R-(1-naphthyl)ethylamino)pyrrolidin-1-yl)phenylacetic acid (112 mg).

Example 4

Transformation of Form B Crystal to Form A Crystal of 4-(3S-(1R-(1-naphthyl)ethylamino)pyrrolidin-1-yl)phenylacetic Acid

[Chem. 27]

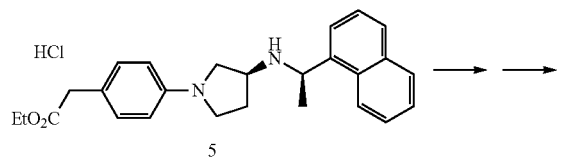

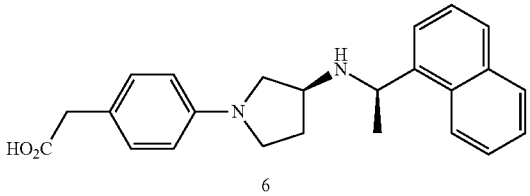

Ethanol (10 mL) and a 2 M aqueous sodium hydroxide solution (7.4 mL) were added to Compound 5 (1.00 g). While stirring, the mixture was heated to 60° C. and was reacted at the same temperature for 30 minutes. The reaction solution was cooled to 25° C., and a 10% aqueous solution of citric acid monohydrate was added dropwise until the pH reached 7.0. To the resultant slurry (pH 7.0) of a form B crystal of 4-(3S-(1R-(1-naphthyl)ethylamino)pyrrolidin-1-yl)phenylacetic acid, a form A crystal was seeded in a ratio of 5 W/W. The mixture was stirred at 60° C. for 3 hours, and the suspended matter was filtered off. Powder X-ray diffractometry showed that the crystal had been transformed into the form A crystal.

Separately, a form A crystal was seeded to the above slurry of the form B crystal in a ratio of 5 W/W. The mixture was stirred at 40° C. for 3 hours and was further stirred at the same temperature for 2.5 days. Thereafter, the suspended matter was filtered off. Powder X-ray diffractometry showed that the crystal had been transformed into the form A crystal.

Example 5

Dimethylacetamide (5 v/w) was added to a form B crystal of 4-(3S-(1R-(1-naphthyl)ethylamino)pyrrolidin-1-yl)phenylacetic acid at 55° C. At the temperature, ethanol (15 v/w) was added dropwise over a period of 2 hours. After the dropwise addition, the solution was cooled to 25° C. and the crystal was filtered off. The crystal obtained was washed with ethanol (3 v/w) twice and was dried under reduced pressure at 60° C. Powder X-ray diffractometry showed that the crystal obtained was form A crystal.

Reference Example 1

Production of 4-(3S-(1R-(1-naphthyl)ethylamino)pyrrolidin-1-yl)phenylacetic Acid (Amorphous)

A suspension of 4-(3S-(1R-(1-naphthyl)ethylamino)pyrrolidin-1-yl)phenylacetic acid (150 mg) in 6 ml of tetrahydrofuran was heated to give a solution. The reaction solution was stirred at room temperature overnight, and then 3 ml of acetone was added. The mixture was stirred at room temperature for 30 minutes. Further, 15 ml of diethyl ether was added thereto and the mixture was stirred at room temperature for 3 hours. Thereafter, the reaction solution was allowed to stand in a refrigerator overnight. The powder precipitated was filtered off and was dried by blowing air at 50° C. overnight to give 4-(3S-(1R-(1-naphthyl)ethylamino)pyrrolidin-1-yl)phenylacetic acid (amorphous, 13 mg, containing 0.1 to 0.2 equivalents of tetrahydrofuran as the residual solvent).

$^1$H NMR (400 MHz, DMSO-$d_6$): δ 8.33 (br d, J=8.2 Hz, 1H), 7.89-8.12 (br, 1H), 7.68-7.89 (br, 2H), 7.30-7.67 (br, 3H), 7.02 (br d, J=7.7 Hz, 2H), 6.41 (br, 2H), 4.75 (br, 1H), 3.60 (m, 0.52H, assigned to THF), 3.37 (s, 2H), 2.80-3.18 (br, 2H), 1.81-2.20 (br, 2H), 1.76 (m, 0.52H, assigned to THF), 1.43 (br, 3H).

Reference Example 2

Production of 4-(3S-(1R-(1-naphthyl)ethylamino) pyrrolidin-1-yl)phenylacetic Acid•1.5 hydrochloride 4 N hydrochloric acid/dioxane solution (200 μL) was added to a suspension of 4-(3S-(1R-(1-naphthyl)ethylamino)pyrrolidin-1-yl)phenylacetic acid (form B crystal, 200 mg) in tetrahydrofuran (5 mL). Further, tetrahydrofuran (5 mL) and 4 N hydrochloric acid/dioxane solution (200 μL) were added thereto. The powder precipitated was filtered off, washed with tetrahydrofuran and diethyl ether, and dried to give 4-(3S-(1R-(1-naphthyl)ethylamino)pyrrolidin-1-yl) phenylacetic acid•1.5 hydrochloride (amorphous, 73 mg, containing 0.2 to 0.3 equivalents of tetrahydrofuran and 0.02 to 0.03 equivalents of diethyl ether as the residual solvents).

Tetrahydrofuran and diethyl ether as the residual solvents were identified by NMR.

Elemental analysis:
(Theoretical values for 1.5HCl salt 0.2THF 0.03Et$_2$O 0.75H$_2$O)
C: 65.16 H: 6.78 N: 6.10 Cl: 11.58
(Measured values)
C: 65.16 H: 6.87 N: 6.15 Cl: 11.47

Reference Example 3

Production of 4-(3S-(1R-(1-naphthyl)ethylamino) pyrrolidin-1-yl)phenylacetic Acid•1.7 hydrochloride A suspension of 4-(3S-(1R-(1-naphthyl)ethylamino)pyrrolidin-1-yl)phenylacetic acid (200 mg) in tetrahydrofuran (30 mL) was heated to give a solution. To the solution, 4 N hydrochloric acid/ethyl acetate solution (280 μL) was added and the reaction solution was partially concentrated. While heating the reaction solution, tetrahydrofuran was added again to dissolve the powder precipitated. While stirring the reaction solution, diethyl ether was added under ice cooling. The powder precipitated was filtered off, washed with diethyl ether, and dried to give 4-(3S-(1R-(1-naphthyl)ethylamino)pyrrolidin-1-yl)phenylacetic acid•1.7 hydrochloride (amorphous, 110 mg, containing 0.2 to 0.3 equivalents of tetrahydrofuran as the residual solvent).

Tetrahydrofuran as the residual solvent was identified by NMR.

Elemental analysis:
(Theoretical values for 1.7HCl salt 0.3THF 1.0H$_2$O)
C: 63.57 H: 6.80 N: 5.88 Cl: 12.66
(Measured values)
C: 63.48 H: 6.80 N: 5.96 Cl: 12.66

Reference Example 4

Production of 4-(3S-(1R-(1-naphthyl)ethylamino) pyrrolidin-1-yl)phenylacetic acid•monohydrochloride 1 mL of acetonitrile was added to 4-(3S-(1R-(1-naphthyl) ethylamino)pyrrolidin-1-yl)phenylacetic acid (form B crystal, 100 mg). The mixture was refluxed, and 0.1 mol/L hydrochloric acid/acetonitrile solution (2.7 mL) was added thereto. The suspension was stirred under reflux for 30 minutes and was thereafter stirred at room temperature overnight. The resultant powder was filtered off, washed with approximately 1 mL of diethyl ether, and then dried under reduced pressure at 40° C. for 3 hours to give 4-(3S-(1R-(1-naphthyl)ethylamino)pyrrolidin-1-yl)phenylacetic acid-monohydrochloride (crystal, 97 mg, containing 0.05 to 0.06 equivalents of acetonitrile and 0.03 to 0.04 equivalents of diethyl ether as the residual solvents).

Acetonitrile and diethyl ether as the residual solvents were identified by NMR.

Elemental analysis:
(Theoretical values for 1HCl salt 0.05CH$_3$CN 0.03Et$_2$O 0.35H$_2$O)
C: 69.01 H: 6.73 N: 6.81 Cl: 8.41
(Measured values)
C: 68.82 H: 6.60 N: 6.93 Cl: 8.75

Reference Example 5

Production of 4-(3S-(1R-(1-naphthyl)ethylamino) pyrrolidin-1-yl)phenylacetic acid•monohydrochloride•monotetrahydrofuran solvate A suspension of 4-(3S-(1R-(1-naphthyl)ethylamino)pyrrolidin-1-yl)phenylacetic acid (form B crystal, 200 mg) in tetrahydrofuran (30 mL) was heated to give a solution. 4 N hydrochloric acid/dioxane solution (280 μL) was added thereto, and the reaction solution was concentrated. The concentrate was dissolved by the addition of tetrahydrofuran, and the solution was allowed to stand for 2 days. The powder precipitated was filtered off, washed with diethyl ether, and then dried to give 4-(3S-(1R-(1-naphthyl)ethylamino)pyrrolidin-1-yl)phenylacetic acid•monohydrochloride•monotetrahydrofuran solvate (crystal, 100 mg).

Elemental analysis:
(Theoretical values for 1HCl salt 1THF 0.15H$_2$O)
C: 69.23 H: 7.32 N: 5.77 Cl: 7.30
(Measured values)
C: 69.17 H: 7.26 N: 5.83 Cl: 7.34

Reference Example 6

Production of 4-(3S-(1R-(1-naphthyl)ethylamino) pyrrolidin-1-yl)phenylacetic Acid monohydrobromide Acetone (42 mL) was added to 4-(3S-(1R-(1-naphthyl) ethylamino)pyrrolidin-1-yl)phenylacetic acid (form A crystal, 100 mg). The mixture was heated at 50° C. to give a solution. 47% Aqueous hydrobromic acid solution (approximately 50 mg) was added, and then heptane (30 mL) was added. While stirring, the mixture was cooled to 30° C., and heptane (5 mL) was further added thereto. The mixture was heated to 50° C., and was stirred for 45 minutes and then at room temperature overnight. The powder precipitated was filtered off, washed with heptane (1 mL), and dried under reduced pressure at 40° C. for 2 hours to give 4-(3S-(1R-(1-naphthyl)ethylamino)pyrrolidin-1-yl)phenylacetic acid-monohydrobromide (crystal, 71 mg).

Elemental analysis:
(Theoretical values for 1HBr salt)
C: 63.30 H: 5.98 N: 6.15 Br: 17.55
(Measured values)
C: 63.19 H: 5.98 N: 6.17 Br: 17.66

Experiment Example 1: Measurement of Diffraction Angles (2θ) of Powder X-Ray Diffraction Peaks FIGS. 1 and 3 show powder X-ray diffraction patterns of form A and form B crystals of Compound (A), respectively.

Tables 1 and 2 describe diffraction angles (2θ) of the powder X-ray diffraction peaks of the form A and form B crystals, respectively.

The data of the properties of the crystals described in Experiment Example 1 were obtained by measurements under the following conditions.

(1) Powder X-Ray Diffractometry
Diffractometer: X'Pert Pro (Panalytical B. V.)
Operating conditions:
X-ray tube: anticathode: copper, tube voltage: 45 kV, tube current: 40 mA
Incident optical system: focusing collecting mirror
Receiving optical system: high-speed semiconductor array detector (X-Celerator)
Sample stage: HTS sample stage (oscillated over 4 mm width in X-axis direction)
Number of scans: 5 scans (while changing the incident angle by −2, −1, 0, 1 and 2°)
Measurement range: 2θ=3 to 40°
(2) Differential Scanning Calorimetry (DSC)
⟨Form A Crystal⟩
Calorimeter: DSC 1 (Mettler-Toledo International Inc.)
Operating Conditions:
Heating rate: 10 K/min
Atmosphere: nitrogen 40 mL/min
⟨Form B Crystal⟩
Calorimeter: DSC 821e (Mettler-Toledo International Inc.)
Operating Conditions:
Heating rate: 10 IC/min
Atmosphere: nitrogen 40 mL/min

TABLE 1

| No. | Diffraction angle (2θ) | d value (Å) | Relative intensity [%] |
|---|---|---|---|
| 1 | 4.1392 | 21.34752 | 8.79 |
| 2 | 8.3105 | 10.63964 | 1.5 |
| 3 | 12.7069 | 6.96661 | 12.95 |
| 4 | 14.1945 | 6.23969 | 4.33 |
| 5 | 14.62 | 6.05904 | 21.18 |
| 6 | 14.7751 | 5.99576 | 8.86 |
| 7 | 16.4002 | 5.40512 | 1.16 |
| 8 | 17.3495 | 5.11146 | 46.85 |
| 9 | 18.6402 | 4.76034 | 100 |
| 10 | 19.0741 | 4.65302 | 66.43 |
| 11 | 20.4864 | 4.33532 | 8.47 |
| 12 | 22.0633 | 4.02891 | 4.68 |
| 13 | 22.4189 | 3.9658 | 6.66 |
| 14 | 22.5666 | 3.94018 | 22.7 |
| 15 | 24.1462 | 3.68588 | 4.54 |
| 16 | 24.521 | 3.63038 | 20.02 |
| 17 | 25.0085 | 3.56071 | 2.54 |
| 18 | 25.185 | 3.53615 | 6.18 |
| 19 | 25.5772 | 3.48282 | 1.25 |
| 20 | 27.2981 | 3.26704 | 1.83 |
| 21 | 28.127 | 3.17262 | 17.6 |
| 22 | 28.4637 | 3.13585 | 3.92 |
| 23 | 29.4275 | 3.0353 | 8.37 |
| 24 | 30.945 | 2.88983 | 7.89 |
| 25 | 31.1409 | 2.87209 | 5.37 |
| 26 | 31.5631 | 2.83463 | 5.2 |
| 27 | 31.855 | 2.80933 | 1.22 |
| 28 | 32.2324 | 2.77729 | 2.28 |
| 29 | 32.9189 | 2.72092 | 3.31 |
| 30 | 33.6933 | 2.66013 | 1.08 |
| 31 | 35.1931 | 2.55013 | 2 |
| 32 | 35.9056 | 2.50115 | 1.13 |
| 33 | 37.6781 | 2.38746 | 1.25 |
| 34 | 38.1112 | 2.36132 | 11.67 |
| 35 | 38.8618 | 2.31743 | 1.89 |
| 36 | 39.6763 | 2.27171 | 1.15 |

TABLE 2

| No. | Diffraction angle (2θ) | d value (Å) | Relative intensity [%] |
|---|---|---|---|
| 1 | 4.1698 | 21.19124 | 12.16 |
| 2 | 8.2648 | 10.69835 | 3.35 |
| 3 | 10.3535 | 8.54428 | 1.1 |
| 4 | 12.0506 | 7.34451 | 1.72 |
| 5 | 12.6064 | 7.02193 | 14.64 |
| 6 | 13.4367 | 6.58986 | 2.83 |
| 7 | 14.4444 | 6.1323 | 9.56 |
| 8 | 14.9031 | 5.94455 | 1.32 |
| 9 | 15.6078 | 5.67773 | 6.61 |
| 10 | 15.8625 | 5.58711 | 32.57 |
| 11 | 17.7447 | 4.99851 | 4.42 |
| 12 | 18.6339 | 4.76192 | 100 |
| 13 | 19.1085 | 4.64472 | 42.24 |
| 14 | 19.6868 | 4.50957 | 13.98 |
| 15 | 20.5409 | 4.32394 | 14.32 |
| 16 | 21.4208 | 4.14828 | 23.46 |
| 17 | 22.0796 | 4.02596 | 1.59 |
| 18 | 22.4944 | 3.95267 | 3.02 |
| 19 | 23.7951 | 3.73946 | 15.91 |
| 20 | 24.2819 | 3.66559 | 15 |
| 21 | 24.7185 | 3.60182 | 2.82 |
| 22 | 25.1763 | 3.53735 | 3.56 |
| 23 | 26.667 | 3.34291 | 1.91 |
| 24 | 27.1188 | 3.28823 | 1.93 |
| 25 | 27.961 | 3.19108 | 26.56 |
| 26 | 28.2599 | 3.158 | 8.29 |
| 27 | 28.8417 | 3.0956 | 2.71 |
| 28 | 29.2769 | 3.05058 | 1.69 |
| 29 | 29.5564 | 3.02236 | 2.23 |
| 30 | 29.954 | 2.98314 | 7.75 |
| 31 | 30.7941 | 2.90365 | 6.55 |
| 32 | 31.2477 | 2.86252 | 3.03 |
| 33 | 31.7231 | 2.82071 | 3.78 |
| 34 | 32.8207 | 2.72883 | 3.24 |
| 35 | 33.9923 | 2.63742 | 2.81 |
| 36 | 35.239 | 2.54691 | 2.26 |
| 37 | 36.6121 | 2.45449 | 2.91 |
| 38 | 38.0171 | 2.36695 | 9.94 |
| 39 | 39.3672 | 2.28883 | 3.02 |

Experiment Example 2: Differential Scanning Calorimetry

The form A crystal and the form B crystal of Compound (A) were each packed into a 40 μL standard aluminum pan and were subjected to the measurement.

As a result, the melting point (the extrapolated onset temperature) of the form A crystal of Compound (A) was observed near 175° C., while the melting point (the extrapolated onset temperature) of the form B crystal of Compound (A) was observed near 166° C.

Experiment Example 3: Determination of Crystal Form Stable at Room Temperature

Equal amounts of the form A crystal and the form B crystal of Compound (A) were added to the same container and were suspended in chloroform. The suspension was stirred at room temperature overnight. Thereafter, the suspended matter was filtered off and was analyzed by powder X-ray diffractometry to determine the type of the crystal form. The result showed that the crystal obtained was of form A. Thus, the form A crystal of Compound (A) was demonstrated to be more stable at room temperature.

Experiment Example 4: Stability Test

Compound (A) and salts thereof were stored under the storage conditions described in Table 3, and the total increase in the amounts of related substance was measured.

TABLE 3

| No | Salt-Compound | Crystal-Solvate | Amorphous (Crystal form) | Storage conditions Temperature | Humidity | Length | Total increase in amounts of related substance (%) |
|---|---|---|---|---|---|---|---|
| 1 | Compound (A) | — | Crystal (Form A) | 60° C. | Natural | 1 Week | 0.03 |
| 2 | Compound (A) | — | Crystal (Form B) | 60° C. | Natural | 1 Week | 0.00 |
| 3 | Compound (A) | — | Amorphous | 60° C. | Natural | 1 Week | 3.32 |
| 4 | Compound (A) | 1.5HCl | Amorphous | 60° C. | Natural | 1 Week | 8.21 |
| 5 | Compound (A) | 1.7HCl | Amorphous | 60° C. | Natural | 1 Week | 8.33 |
| 6 | Compound (A) | 1HBr | Crystal | 60° C. | Natural | 1 Week | 0.21 |
| 7 | Compound (A) | 1HCl | Crystal | 60° C. | Natural | 1 Week | 0.18 |
| 8 | Compound (A) | 1HCl•1THF | Crystal | 60° C. | Natural | 1 Week | 0.75 |
| 9 | Compound (A) | — | Crystal (Form A) | 60° C. | 75% RH | 1 Week | 0.01 |
| 10 | Compound (A) | — | Crystal (Form B) | 60° C. | 75% RH | 1 Week | 0.00 |
| 11 | Compound (A) | — | Amorphous | 60° C. | 75% RH | 1 Week | 14.16 |
| 12 | Compound (A) | 1.5HCl | Amorphous | 60° C. | 75% RH | 1 Week | 3.11 |
| 13 | Compound (A) | 1.7HCl | Amorphous | 60° C. | 75% RH | 1 Week | 3.06 |
| 14 | Compound (A) | 1HBr | Crystal | 60° C. | 75% RH | 1 Week | 0.13 |
| 15 | Compound (A) | 1HCl | Crystal | 60° C. | 75% RH | 1 Week | 1.02 |
| 16 | Compound (A) | 1HCl•1THF | Crystal | 60° C. | 75% RH | 1 Week | 1.04 |

As described in Table 3, the form A and form B crystals of Compound (A) did not show a marked increase in the amounts of related substance and thus these crystal forms were demonstrated to have good storage stability.

In contrast, the amounts of related substance were significantly increased in amorphous Compound (A), amorphous Compound (A)•1.5 hydrochloride and amorphous Compound (A)•1.7 hydrochloride. Further, an increase in the amounts of related substance was observed in Compound (A)•monohydrobromide, Compound (A)•monohydrochloride and Compound (A)•monohydrochloride•monotetrahydrofuran solvate.

Storage of Compound (A)•monohydrochloride•monotetrahydrofuran solvate under the conditions described in No. 16 of Table 3 resulted in the conversion thereof into Compound (A)•monohydrochloride (crystal).

INDUSTRIAL APPLICABILITY

The novel crystals of 4-(3S-(1R-(1-naphthyl)ethylamino)pyrrolidin-1-yl)phenylacetic acid exhibit excellent storage stability. In particular, the form A crystal can exist highly stably in a wide range of temperatures including room temperature, and therefore is useful as a pharmaceutical ingredient.

Further, the processes for producing crystals of 4-(3S-(1R-(1-naphthyl)ethylamino)pyrrolidin-1-yl)phenylacetic acid are industrially advantageous processes capable of producing the crystals in good yield and through short step.

The invention claimed is:

1. A form A crystal of 4-(3S-(1R-(1-naphthyl)ethylamino)pyrrolidin-1-yl)phenylacetic acid showing peaks at 17.3°±0.2° and 22.6°±0.2° as diffraction angles expressed as 2θ in the powder X-ray diffraction spectrum.

2. The form A crystal of 4-(3S-(1R-(1-naphthyl)ethylamino)pyrrolidin-1-yl)phenylacetic acid according to claim 1, of which a powder X-ray diffraction spectrum has a pattern illustrated in FIG. 1.

3. The form A crystal of 4-(3S-(1R-(1-naphthyl)ethylamino)pyrrolidin-1-yl)phenylacetic acid according to claim 1, having a melting point of 174 to 177° C. as measured by differential scanning calorimetry.

4. A form B crystal of 4-(3S-(1R-(1-naphthyl)ethylamino)pyrrolidin-1-yl)phenylacetic acid showing peaks at 15.9°±0.2° and 21.4°±0.20 as diffraction angles expressed as 2θ in the powder X-ray diffraction spectrum.

5. The form B crystal of 4-(3S-(1R-(1-naphthyl)ethylamino)pyrrolidin-1-yl)phenylacetic acid according to claim 4, of which a powder X-ray diffraction spectrum has a pattern illustrated in FIG. 3.

6. The form B crystal of 4-(3S-(1R-(1-naphthyl)ethylamino)pyrrolidin-1-yl)phenylacetic acid according to claim 4, having a melting point of 164 to 167° C. as measured by differential scanning calorimetry.

7. A pharmaceutical composition comprising the crystal according to claim 1, and a pharmacologically acceptable carrier.

8. A process for producing the form A crystal of 4-(3S-(1R-(1-naphthyl)ethylamino)pyrrolidin-1-yl)phenylacetic acid according to claim 1, comprising crystallizing 4-(3S-(1R-(1-naphthyl)ethylamino)pyrrolidin-1-yl)phenylacetic acid in methanol, ethanol, isopropanol, or water in the presence of a base by adding an acid at 50 to 70° C.

9. A process for producing the form B crystal of 4-(3S-(1R-(1-naphthyl)ethylamino)pyrrolidin-1-yl)phenylacetic acid according to claim 4, comprising rapidly crystallizing 4-(3S-(1R-(1-naphthyl)ethylamino)pyrrolidin-1-yl)phenylacetic acid in methanol, ethanol, isopropanol, or water in the presence of a base by adding an acid at 20 to 40° C.

10. A process for producing the form A crystal of 4-(3S-(1R-(1-naphthyl)ethylamino)pyrrolidin-1-yl)phenylacetic acid according to claim 1, comprising seeding a form A crystal to a slurry of a form B crystal of 4-(3S-(1R-(1-naphthyl)ethylamino)pyrrolidin-1-yl)phenylacetic acid and crystallizing the form A crystal at 40 to 70° C., or dissolving a form B crystal into a solution comprising a good solvent and a poor solvent at 40 to 60° C. and then recrystallizing the form A crystal at 20 to 25° C., wherein the good solvent is dimethylsulfoxide or dimethylacetamide, and wherein the poor solvent is methanol, ethanol, isopropanol, acetone, toluene, methyl t-butyl ether, methyl ethyl ketone, methyl isobutyl ketone, acetonitrile, ethyl acetate, or water.

11. A pharmaceutical composition comprising the crystal according to claim 4, and a pharmacologically acceptable carrier.

* * * * *